(12) United States Patent
Yao et al.

(10) Patent No.: US 11,684,916 B2
(45) Date of Patent: Jun. 27, 2023

(54) CHIP FOR POLYMERASE CHAIN REACTION, METHOD OF OPERATION CHIP, AND REACTION DEVICE

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Wenliang Yao, Beijing (CN); Nan Zhao, Beijing (CN); Haochen Cui, Beijing (CN); Peizhi Cai, Beijing (CN); Fengchun Pang, Beijing (CN); Yue Geng, Beijing (CN); Le Gu, Beijing (CN); Yuelei Xiao, Beijing (CN); Hui Liao, Beijing (CN); Yingying Zhao, Beijing (CN); Chuncheng Che, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 599 days.

(21) Appl. No.: 16/632,934

(22) PCT Filed: Jan. 9, 2019

(86) PCT No.: PCT/CN2019/071016
§ 371 (c)(1),
(2) Date: Jan. 22, 2020

(87) PCT Pub. No.: WO2020/142938
PCT Pub. Date: Jul. 16, 2020

(65) Prior Publication Data
US 2021/0060556 A1 Mar. 4, 2021

(51) Int. Cl.
*B01L 3/00* (2006.01)
*C12Q 1/686* (2018.01)

(52) U.S. Cl.
CPC ........ *B01L 3/502715* (2013.01); *C12Q 1/686* (2013.01); *B01L 2300/0645* (2013.01); *B01L 2300/1827* (2013.01)

(58) Field of Classification Search
CPC ......... B01L 3/502715; B01L 3/502792; B01L 2200/147; B01L 2300/1827; B01L 7/525;
(Continued)

(56) References Cited

U.S. PATENT DOCUMENTS 7,943,348 B2    5/2011  Cho et al.
8,425,861 B2 *  4/2013  Selden ............... G01N 21/6402
                                                 435/303.1
(Continued)

FOREIGN PATENT DOCUMENTS

CN      1680574 A    10/2005
CN    102899238 A     1/2013
(Continued)

*Primary Examiner* — Shogo Sasaki
(74) *Attorney, Agent, or Firm* — Collard & Roe, P.C.

(57) ABSTRACT

A chip for polymerase chain reaction, a method of operating a chip for polymerase chain reaction, and a reaction device are provided. The chip includes: a sample adding region, a mixing region, a temperature cycling region in a sequential arrangement, and at least one driving unit group. The at least one driving unit group includes a plurality of driving units and is configured to drive a liquid drop to move and sequentially pass through the sample adding region, the mixing region, and the temperature cycling region.

19 Claims, 6 Drawing Sheets

(58) Field of Classification Search
CPC ............ B01L 2300/0645; C12Q 1/686; C12Q 2565/607
See application file for complete search history.

(56) References Cited

U.S. PATENT DOCUMENTS 9,421,555 B2 * 8/2016 Lee .................... B03C 1/288
11,376,583 B2 * 7/2022 Faltin .................. B01L 7/525

FOREIGN PATENT DOCUMENTS

| CN | 103695308 A | 4/2014 |
| CN | 107937265 A | 4/2018 |
| CN | 108034703 A | 5/2018 |

* cited by examiner

CHIP FOR POLYMERASE CHAIN REACTION, METHOD OF OPERATION CHIP, AND REACTION DEVICE

CROSS REFERENCE TO RELATED APPLICATIONS

This application is the National Stage of PCT/CN2019/071016 filed on Jan. 9, 2019, the disclosure of which is incorporated by reference.

TECHNICAL FIELD

Embodiments of the present disclosure relate to a chip for polymerase chain reaction, a method of operating a chip for polymerase chain reaction, and a reaction device.

BACKGROUND

Polymerase chain reaction (PCR) is a molecular biology technology used for amplifying specific deoxyribonucleic acid (DNA) segments. The double-stranded structure of the DNA segment is annealed at a high temperature to form a single-stranded structure, primers and single strands refold according to the principle of complementary base pairing at a low temperature, and nucleobase extension is implemented at an optimal temperature of DNA polymerase. The DNA segment can be amplified by a great quantity through a plurality of temperature cycling amplification processes, and the temperature cycling amplification process includes an annealing process, a refolding process, and an extending process.

SUMMARY

At least one embodiment of the present disclosure provides a chip for polymerase chain reaction, which includes: a sample adding region, a mixing region, and a temperature cycling region in a sequential arrangement; and at least one driving unit group. The at least one driving unit group includes a plurality of driving units, and is configured to drive a liquid drop to move and sequentially pass through the sample adding region, the mixing region, and the temperature cycling region.

For example, in the chip provided by an embodiment of the present disclosure, each of the at least one driving unit group includes: a first driving unit sub-group, in the temperature cycling region and configured to drive the liquid drop to cyclically move in the temperature cycling region; a second driving unit sub-group, in the mixing region and configured to drive the liquid drop to cyclically move in the mixing region; and a third driving unit sub-group, in the sample adding region and configured to drive the liquid drop to move in the sample adding region.

For example, in the chip provided by an embodiment of the present disclosure, the first driving unit sub-group includes a plurality of driving units arranged in a ring.

For example, the chip provided by an embodiment of the present disclosure further includes at least one first liquid container and at least one second liquid container, and the first liquid container and the second liquid container are in the sample adding region, and are configured to store different liquids and provide the liquid drop.

For example, in the chip provided by an embodiment of the present disclosure, the at least one driving unit group includes a first driving unit group and a second driving unit group, and the first driving unit group and the second driving unit group are configured to obtain the liquid drop from one same first liquid container.

For example, in the chip provided by an embodiment of the present disclosure, the second driving unit sub-group is further configured to allow a first liquid drop from the first liquid container to be mixed with a second liquid drop from the second liquid container.

For example, in the chip provided by an embodiment of the present disclosure, the driving unit includes a first substrate and a second substrate opposite to each other, and a driving electrode. A flowing space for the liquid drop is between the first substrate and the second substrate, and the driving electrode is on the first substrate.

For example, in the chip provided by an embodiment of the present disclosure, the driving unit further includes a first insulating layer and a first hydrophobic layer, the first insulating layer and the first hydrophobic layer are sequentially stacked on the first substrate, and the driving electrode is on a side, close to the second substrate, of the first substrate, and is covered by the first insulating layer and the first hydrophobic layer.

For example, the chip provided by an embodiment of the present disclosure further includes a second insulating layer, a common electrode layer, and a second hydrophobic layer; the second insulating layer, the common electrode layer, and the second hydrophobic layer are sequentially stacked on the second substrate; and the second hydrophobic layer is closer to the first substrate.

For example, the chip provided by an embodiment of the present disclosure further includes a plurality of temperature control components, the plurality of temperature control components include a first temperature control component, a second temperature control component, and a third temperature control component, the temperature cycling region includes a plurality of temperature regions in a sequential arrangement, and the plurality of temperature regions include a first temperature region, a second temperature region, and a third temperature region. The first temperature control component is in the first temperature region and is configured to allow the first temperature region to stay at a first temperature, so as to enable a gene segment in the liquid drop to be annealed, the second temperature control component is in the second temperature region and is configured to allow the second temperature region to stay at a second temperature, so as to enable the gene segment in the liquid drop to refold, and the third temperature control component is in the third temperature region and is configured to allow the third temperature region to stay at a third temperature, so as to enable the gene segment in the liquid drop to extend.

For example, in the chip provided by an embodiment of the present disclosure, each of the temperature control components includes a heating electrode and a temperature sensing electrode, the heating electrode is on the second substrate or the first substrate and is configured to release heat, and the temperature sensing electrode is on the second substrate or the first substrate and is configured to sense a temperature.

For example, in the chip provided by an embodiment of the present disclosure, the heating electrode is in a broken line shape.

For example, in the chip provided by an embodiment of the present disclosure, the temperature sensing electrode is insulated from the heating electrode, and the temperature sensing electrode is in a pattern formed by the heating electrode.

For example, in the chip provided by an embodiment of the present disclosure, a part of the driving units of the driving unit group are in the temperature cycling region, and are outside the first temperature region, the second temperature region, and the third temperature region.

For example, the chip provided by an embodiment of the present disclosure further includes a liquid collecting region, and the at least one driving unit group is further configured to drive the liquid drop to move into the liquid collecting region after the liquid drop passes through the temperature cycling region.

For example, in the chip provided by an embodiment of the present disclosure, the second substrate is a transparent substrate.

At least one embodiment of the present disclosure further provides a reaction device, which includes the chip provided by any one of the embodiments of the present disclosure, and further includes a control unit; and the control unit is configured to apply electric signals to driving electrodes of the driving units to control the liquid drop to move.

For example, the reaction device provided by an embodiment of the present disclosure further includes a temperature control unit, and the temperature control unit is configured to acquire a detection signal of a temperature sensing electrode of the chip and control a working state of a heating electrode of the chip, so as to implement temperature control.

At least one embodiment of the present disclosure further provides a method of operating the chip provided by any one of the embodiments of the present disclosure, and the method includes: applying electric signals to driving electrodes of the driving units to allow the liquid drop to move and sequentially pass through the sample adding region, the mixing region, and the temperature cycling region.

For example, the method provided by an embodiment of the present disclosure further includes: using a temperature sensing electrode of the chip to detect temperatures of a plurality of temperature regions in the temperature cycling region, and controlling a working state of a heating electrode of the chip to allow the temperatures of the plurality of temperature regions to reach predetermined temperatures, respectively.

BRIEF DESCRIPTION OF THE DRAWINGS

In order to clearly illustrate the technical solution of the embodiments of the present disclosure, the drawings of the embodiments will be briefly described in the following. It is obvious that the described drawings in the following are only related to some embodiments of the present disclosure and thus are not limitative of the present disclosure.

DETAILED DESCRIPTION

Figure 1:
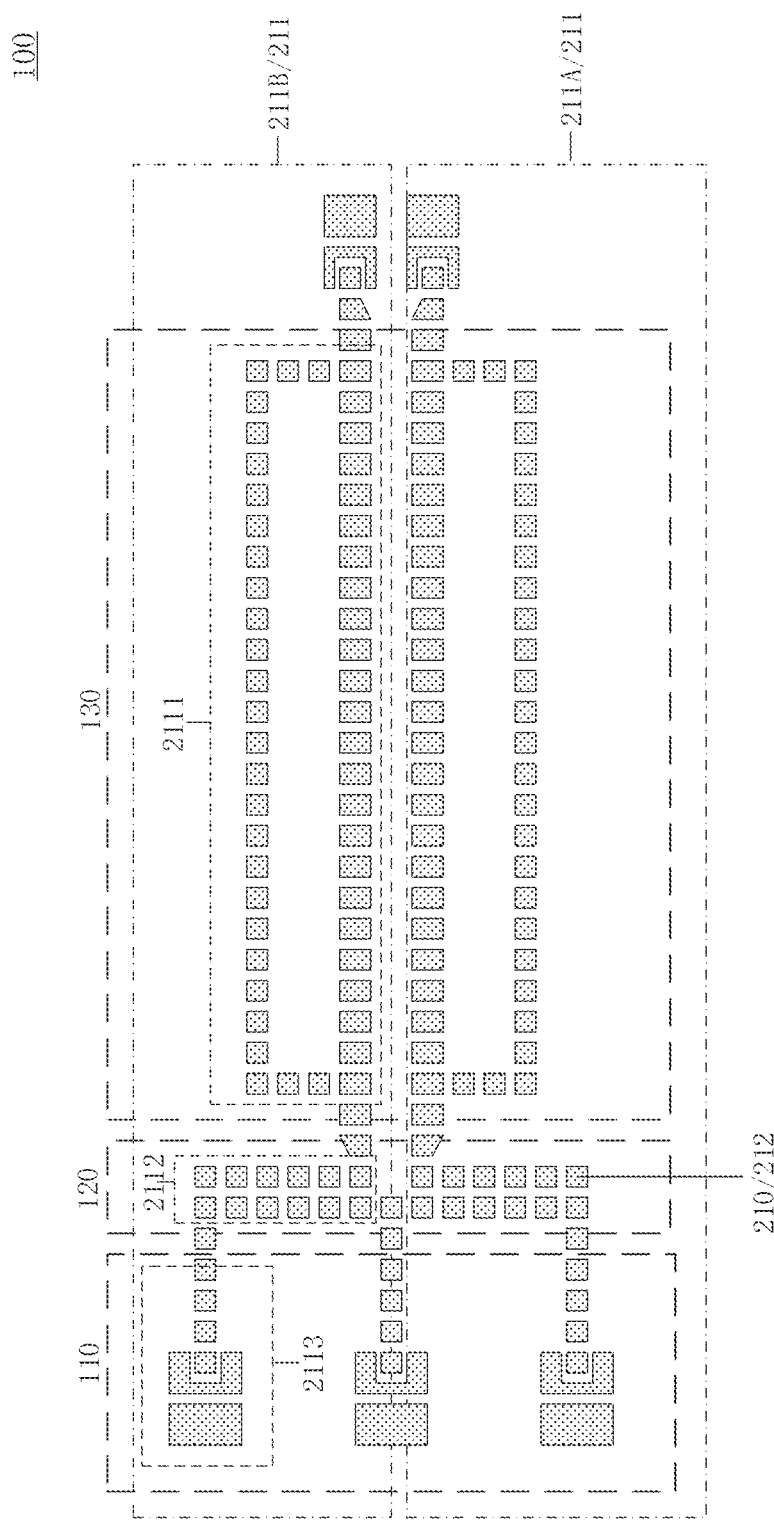
FIG. 1 is a planar schematic diagram of a chip provided by an embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", "coupled", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

The PCR microfluidic chip is a new generation of PCR technology, and usually includes a microcavity type and a flowing type. The PCR chip of the microcavity type implements heating and cooling the reaction liquid in the microcavity by heating and cooling the entire chip, thereby implementing the temperature cycling amplification process of annealing, refolding and extending. The PCR chip of the flowing type uses a peripheral device such as a syringe pump to drive the reaction liquid to flow at a certain speed in the channel and sequentially pass through different temperature regions (for example, three different temperature regions), and the three temperature regions are maintained at a constant temperature, respectively. The reaction liquid passes through different regions at a certain speed, thereby implementing maintaining time of an annealing-refolding-extending process.

The PCR chip of the microcavity type needs to use the Peltier effect to implement temperature control, thereby including corresponding thermal conduction systems and control systems, and increasing the complexity of the peripheral devices. The PCR chip of the flowing type needs such as the syringe pump to drive the liquid to pass through different temperature regions in the channel, and the peripheral devices are complicated and it is easy to cause pollution, thereby affecting the accuracy and repeatability of the detection result. Moreover, whether the PCR chip of the microcavity type or the PCR chip of the flowing type needs to prepare the reaction liquid in advance. For example, the preparation of the reaction liquid includes processes such as the preparation of the reaction system, sample mixing, and the like, and these processes need to be manually performed in different spaces by operators. Therefore, the preparation process is complicated, and the time cost and labor cost are high.

In a case where the traditional PCR amplification instrument is used for thermal cycling amplification, the PCR amplification instrument is large in size and inconvenient to carry, so that it is difficult to satisfy requirements for real time detection.

At least one embodiment of the present disclosure provides a chip for polymerase chain reaction (PCR), a method of operating a chip for polymerase chain reaction, and a reaction device. The chip allows processes such as sample mixing, temperature cycling amplification, and product collection during the nucleic acid amplification to be integrated, thereby lowering requirements for experimental environment, reducing manual operations, providing a flowing temperature cycling function, simplifying a system structure and an apparatus volume, reducing operating costs, and contributing to implementation of real time detection.

Hereinafter, the embodiments of the present disclosure are described in detail with reference to the accompanying drawings. It should be noted that the same reference numerals in different drawings are used to indicate the same components described.

At least one embodiment of the present disclosure provides a chip for polymerase chain reaction (PCR). The chip includes a sample adding region, a mixing region, and a temperature cycling region in a sequential arrangement, and at least one driving unit group. The at least one driving unit group includes a plurality of driving units and is configured to drive a liquid drop to move and sequentially pass through the sample adding region, the mixing region, and the temperature cycling region.

FIG. 1 is a planar schematic diagram of a chip provided by an embodiment of the present disclosure. As illustrated in FIG. 1, a chip 100 includes a sample adding region 110, a mixing region 120, and a temperature cycling region 130 in a sequential arrangement. The chip 100 further includes at least one driving unit group 211 (for example, a first driving unit group 211A and a second driving unit group 211B). The at least one driving unit group 211 includes a plurality of driving units 210 and is configured to drive a liquid drop to move according to a driving signal, for example, to drive the liquid drop to sequentially pass through the sample adding region 110, the mixing region 120, and the temperature cycling region 130. For example, the chip 100 is used for PCR.

For example, the sample adding region 110 is configured for adding a sample, that is, for separating a sample liquid and a reaction system liquid which are stored in a liquid container into liquid drops, such as microliter-scale liquid drops, respectively. For example, the sample liquid includes DNA segments to be amplified, and the reaction system liquid includes specific sequence primers, DNA polymerases, deoxyribonucleoside triphosphate, a buffer liquid, probes, etc. The mixing region 120 is configured to allow the liquid drop from the sample liquid to be mixed with the liquid drop from the reaction system liquid, and the mixed liquid drop is the reaction liquid. The temperature cycling region 130 is configured to allow the liquid drop of the reaction liquid to perform an annealing-refolding-extending temperature cycling amplification process, so as to perform the amplification reaction. For example, one or more temperature cycling amplification processes may be performed, and the embodiments of the present disclosure are not limited in this aspect.

For example, each driving unit group 211 includes a first driving unit sub-group 2111, a second driving unit sub-group 2112, and a third driving unit sub-group 2113. The first driving unit sub-group 2111 is located in the temperature cycling region 130 and is configured to drive the liquid drop to cyclically move in the temperature cycling region 130. The second driving unit sub-group 2112 is located in the mixing region 120 and is configured to drive the liquid drop to cyclically move in the mixing region 120. The third driving unit sub-group 2113 is located in the sample adding region 110 and is configured to drive the liquid drop to move in the sample adding region 110.

For example, the plurality of driving units 210 are arranged along the sample adding region 110, the mixing region 120, and the temperature cycling region 130, and for example, form a liquid drop moving path. In some embodiments of the present disclosure, a control unit or a control circuit (not illustrated in the figure) sequentially applies driving signals to the driving electrodes 212 of the plurality of driving units 210 to drive the liquid drop to move along the liquid drop moving path, so as to allow the liquid drop to sequentially pass through the sample adding region 110, the mixing region 120, and the temperature cycling region 130, thereby implementing integration of processes such as sample mixing and temperature cycling amplification, lowering requirements for experimental environment, and reducing manual operations. For example, in some embodiments of the present disclosure, the movement of the liquid drop may be controlled by the driving electrodes 212 in a common electro-wetting manner, and the driving signals applied to the driving electrodes 212 may be a set of voltage signals. The principle (for example, the principle of the electro-wetting effect) of using the driving electrodes 212 to drive the liquid drop to move can be referred to the conventional design, which is not described in detail here.

For example, the driving electrode 212 may be in any shape such as a square, a rectangle, a trapezoid, and may be in a regular polygon or an irregular polygon. The embodiments of the present disclosure are not limited in this aspect. The number and size of the driving electrodes 212 are also not limited, and can be determined according to practical requirements, such as the size of the chip 100, the size of the liquid drop, the required length of the liquid drop moving path, etc. For example, the shapes and sizes of respective driving electrodes 212 may be the same or different, as long as the liquid drop can be driven to move. The embodiments of the present disclosure are not limited in this aspect.

Figure 2:
FIG. 2 is a schematic diagram of a liquid drop moving path in a chip provided by an embodiment of the present disclosure.

FIG. 2 is a schematic diagram of a liquid drop moving path in a chip provided by an embodiment of the present disclosure. As illustrated in FIG. 2, the plurality of driving units 210 form two liquid drop moving paths, and the two liquid drop moving paths do not cross each other. That is, the first driving unit group 211A forms one liquid drop moving path, the second driving unit group 211B forms another liquid drop moving path, and the two liquid drop moving paths do not cross each other. For example, in an example, a plurality of driving units 210 in the first driving unit group 211A form a first liquid drop moving path 310 (as illustrated by a solid line with an arrow in FIG. 2), and a plurality of driving units 210 in the second driving unit group 211B form a second liquid drop moving path 320 (as illustrated by a dotted line with an arrow in FIG. 2). In the first liquid drop moving path 310 and the second liquid drop moving path 320, the liquid drops can be driven by the driving units 210 and sequentially pass through the sample adding region 110, the mixing region 120, and the temperature cycling region 130, respectively, and the first liquid drop moving path 310 and the second liquid drop moving path 320 do not cross each other.

It should be noted that, by providing two liquid drop moving paths, the DNA segment to be amplified and the quality control material can be amplified simultaneously without interference, that is, the DNA segment to be amplified and the quality control material can move through different liquid drop moving paths, respectively. For example, the quality control material may be a DNA segment of known categories. In this way, the DNA segment to be amplified and the quality control material are amplified under the same environmental conditions, so as to facilitate determining whether the amplification process is effective during subsequent detection. Certainly, the embodiments of the present disclosure are not limited to the above cases. For example, driving unit groups 211 of any number such as 3, 4, and 5 may further be provided (that is, liquid drop moving paths of any number such as 3, 4, and 5 may further be provided), and the number can be determined according to the number of types of DNA segments to be amplified, so as to implement simultaneous detection of a plurality of samples, thereby avoiding cross-contamination, improving detection efficiency, and reducing detection costs.

For example, the chip 100 further includes at least one first liquid container 220 and at least one second liquid container 230. For example, the first liquid container 220 and the second liquid container 230 are located in the sample adding region 110 and are configured to store different liquids and provide liquid drops. For example, in an example, there are two second liquid containers 230, which are a second liquid container 231 and a second liquid container 232, respectively. For example, the first liquid container 220 is used to store the reaction system liquid, the second liquid container 231 is used to store the sample liquid including the DNA segment to be amplified, and the second liquid container 232 is used to store the quality control material liquid. By applying driving signals to the driving electrodes 212 of the driving units 210, the liquid drops can be separated from each liquid container and enter the liquid drop moving path formed by respective driving unit groups 211. For example, the first driving unit group 211A and the second driving unit group 211B are configured to obtain the liquid drops of the reaction system liquid from one same first liquid container 220.

For example, the second driving unit sub-group 2112 of each driving unit group 211 is further configured to allow a first liquid drop from the first liquid container 220 to be mixed with a second liquid drop from the second liquid container 220. For example, as illustrated in FIG. 2, the mixing region 120 at least includes a first mixing region 121 and a second mixing region 122. The second driving unit sub-group 2112 of the first driving unit group 211A is located in the first mixing region 121, and the second driving unit sub-group 2112 of the second driving unit group 211B is located in the second mixing region 122. The second driving unit sub-group 2112 of the first driving unit group 211A is configured to allow a first liquid drop 410 from the first liquid container 220 to be mixed with a second liquid drop 420 from the second liquid container 231, and the second driving unit sub-group 2112 of the second driving unit group 211B is configured to allow the first liquid drop 410 from the first liquid container 220 to be mixed with a second liquid drop 430 from the second liquid container 232. For example, in an example, in the first mixing region 121, the first liquid drop 410 from the first liquid container 220 and the second liquid drop 420 from the second liquid container 231 are mixed, so as to obtain the liquid drop of the reaction liquid including the DNA segment to be amplified; and in the second mixing region 122, the first liquid drop 410 from the first liquid container 220 and the second liquid drop 430 from the second liquid container 232 are mixed, so as to obtain the liquid drop of the reaction liquid including the quality control material.

For example, the second driving unit sub-group 2112 includes a plurality of driving units 210 arranged in a ring to form a loop. For example, as illustrated in FIG. 2, in an example, the first liquid drop moving path 310 has a second loop 312 in the mixing region 120 (e.g., the first mixing region 121), and the liquid drop may cyclically move along the second loop 312 in the first mixing region 121, for example, from a point P1 to a point P2 in a direction illustrated by the solid line with the arrow. Similarly, the second liquid drop moving path 320 also has a corresponding second loop 312 in the second mixing region 122. By setting the second loop 312, the liquid drop from the sample liquid or the liquid drop from the quality control material liquid can be sufficiently mixed with the liquid drop from the reaction system liquid, so as to be uniformly mixed.

For example, the temperature cycling region 130 includes a plurality of temperature regions in a sequential arrangement, the plurality of temperature regions include a first temperature region 131, a second temperature region 132, and a third temperature region 133, and temperatures of the first temperature region 131, the second temperature region 132 and the third temperature region 133 may be controlled to be different from each other. For example, in an example, the first temperature region 131 is configured to maintain at a first temperature (e.g., about 95° C.), so as to enable a gene segment (i.e., the DNA segment to be amplified) in the liquid drop to be annealed, the second temperature region 132 is configured to maintain at a second temperature (e.g., about 65° C.), so as to enable the gene segment in the liquid drop to refold, and the third temperature region 133 is configured to maintain at a third temperature (e.g., about 72° C.), so as to enable the gene segment in the liquid drop to extend.

In a case where the liquid drop moves along the liquid drop moving path, the liquid drop can sequentially pass through the first temperature region 131, the second temperature region 132, and the third temperature region 133, so as to implement the annealing-refolding-extending temperature cycling amplification process of the gene segment in the liquid drop. For example, the speed of the liquid drop passing through each temperature region and the time of the liquid drop staying in each temperature region can be controlled to control the maintaining time of the liquid drop at each temperature, thereby effectively controlling the temperature cycling amplification process and allowing the gene segment in the liquid drop to be greatly amplified. It should be noted that, in the embodiments of the present disclosure, the temperatures of the first temperature region 131, the second temperature region 132, and the third temperature region 133 are not limited to 95° C., 65° C., and 72° C., and may be other suitable temperatures, which may be determined according to the suitable temperature of the DNA polymerases in the reaction liquid. The embodiments of the present disclosure are not limited in this aspect.

For example, the first driving unit sub-group 2111 includes a plurality of driving units 210 arranged in a ring to form a loop. For example, as illustrated in FIG. 2, in an example, the first liquid drop moving path 310 has a first loop 311 in the temperature cycling region 130, and the liquid drop can cyclically move along the first loop 311 in the temperature cycling region 130, for example, from a point M1 to a point M2 in a direction illustrated by the solid line with the arrow. Similarly, the second liquid drop moving path 320 also has a corresponding first loop 311 in the temperature cycling region 130. By setting the first loop 311, the liquid drop can be driven to pass through the first temperature region 131, the second temperature region 132, and the third temperature region 133 multiple times, so that a plurality of temperature cycling amplification processes can be performed in the temperature cycling region 130 and the DNA segment to be amplified can be amplified multiple times to reach a desired number.

For example, the chip 100 further includes a liquid collecting region 140. The plurality of driving units 210 are further arranged along the liquid collecting region 140, and the driving unit group 211 is further configured to drive the liquid drop to move into the liquid collecting region 140 after the liquid drop passes through the temperature cycling region 130. The liquid collecting region 140 is used to collect the amplified liquid drop for further subsequent detection. For example, according to the number of the driving unit groups 211 (that is, the number of the liquid drop moving paths), liquid collecting containers of the same number can be provided in the liquid collecting region 140, so as to implement collection of different liquid drops.

In the following, the process of performing PCR amplification by using the chip 100 is exemplarily described.

For example, in an example, a pipetting gun is first used to add the sample liquid, which includes the DNA segment to be amplified, and the reaction system liquid into the liquid containers, respectively. For example, the sample liquid including the DNA segment to be amplified is added into the second liquid container 231, and the reaction system liquid is added into the first liquid container 220. Each region of the chip 100 is filled with fluorinated oil. Then, the first liquid drop 410 and the second liquid drop 420 are generated and moved to the first mixing region 121 under action of the driving signals applied to the driving electrodes 212 of the driving units 210, and are in a fast circular motion (for example, 5 to 10 circles) along the direction indicated by the arrow in the second loop 312, so as to implement sufficient mixing. Subsequent to the mixing, the liquid drop of the reaction liquid including the DNA segment to be amplified is obtained, and the liquid drop moves into the temperature cycling region 130. By applying the driving signals to the driving electrodes 212 of the driving units 210, the liquid drop is controlled to sequentially pass through the first temperature region 131, the second temperature region 132, and the third temperature region 133, that is, through the annealing-refolding-extending region, and the liquid drop stays in each temperature region for different time according to practical requirements, so as to improve the amplification efficiency.

After one temperature cycle, the liquid drop returns along the first loop 311 and starts the next cycle. After the temperature cycles of predetermined number, the liquid drop moves into the liquid collecting region 140 to implement liquid drop collection and subsequent detection. The liquid drops are isolated from each other in the oil bath, thereby avoiding sample evaporation and aerosol cross-contamination during the temperature cycling amplification process, and ensuring the accuracy of the result. For example, the quality control material liquid may further be added to the second liquid container 232, and the moving path and operation process of the quality control material liquid in the chip 100 are similar to those of the sample liquid, which are not described in detail here. For example, the driving signals applied to the driving electrodes 212 of the driving units 210 are similar to the driving signals in the common electro-wetting manner, which are not described in detail here.

The chip 100 allows processes such as sample mixing, temperature cycling amplification, and product collection during nucleic acid amplification to be integrated, thereby lowering requirements for experimental environment, reducing manual operations, providing a flowing temperature cycling function, simplifying a system structure and an apparatus volume, reducing operating costs, and contributing to implementation of real time detection.

Figure 3:
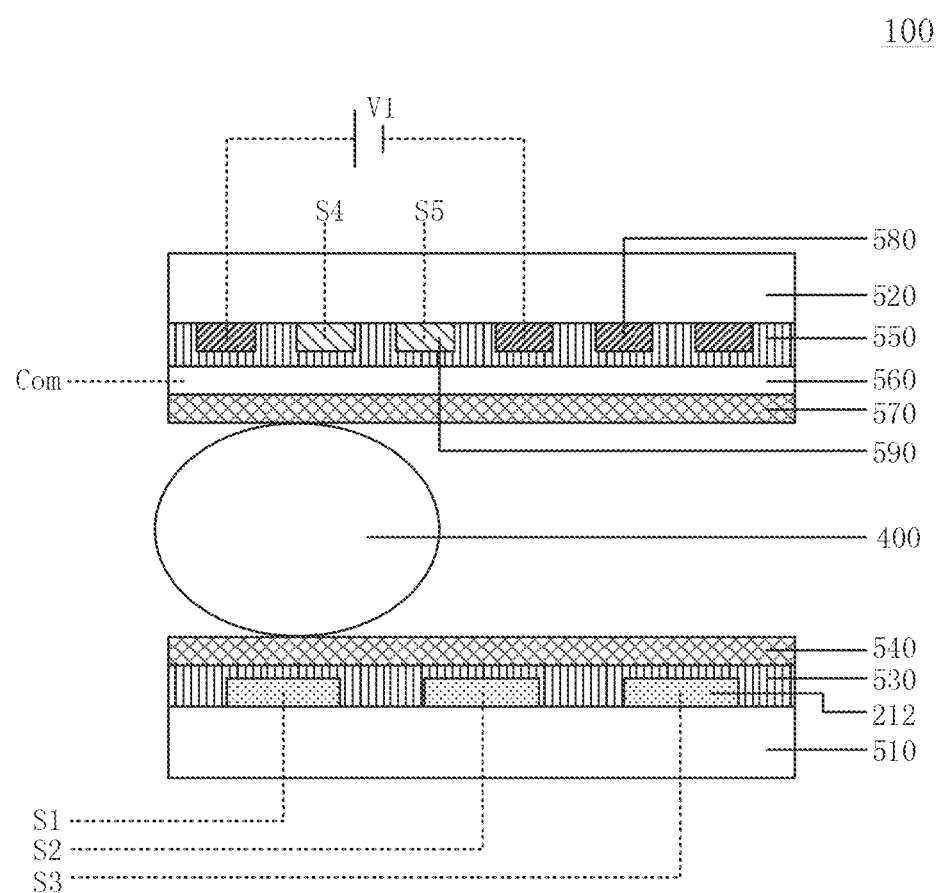
FIG. 3 is a cross-sectional diagram of the chip in FIG. 2 along an A-A' direction provided by an embodiment of the present disclosure.

FIG. 3 is a cross-sectional diagram of the chip in FIG. 2 along an A-A' direction provided by an embodiment of the present disclosure. For convenience of description, the liquid drop is illustrated in the figure, and the plurality of driving units 210 are further illustrated. As illustrated in FIG. 3, in the chip 100, the driving unit 210 includes a first substrate 510 and a second substrate 520 opposite to each other. For example, a flowing space for the liquid drop is between the first substrate 510 and the second substrate 520. The driving unit 210 further includes a driving electrode 212, and the driving electrode 212 is disposed on the first substrate 510. For example, a liquid drop 400 is the liquid drop obtained subsequent to uniform mixing.

The first substrate 510 and the second substrate 520 further provide functions such as supporting and protection. For example, the two substrates can be combined at the edge position by using materials such as a sealant and an optical adhesive, and a certain space can be reserved between the two substrates. For example, the first substrate 510 and/or the second substrate 520 may be a plastic substrate, a glass substrate, or a silicon substrate, or may be other suitable substrates, and the embodiments of the present disclosure are not limited in this aspect. For example, in a case where the glass substrate is used, the cost is lower; and in a case where the silicon substrate is used, the performance is better.

For example, in an example, the second substrate 520 is a transparent substrate, such as a glass substrate, a plastic substrate, etc. Because the second substrate 520 is transparent, after the liquid drop completes the temperature cycling amplification process, the chip 100 can be directly used for subsequent optical detection, thereby eliminating the collecting process of the liquid drop, improving the detection efficiency, and expanding the application range of the chip 100.

The driving unit 210 further includes a first insulating layer 530 and a first hydrophobic layer 540. The first insulating layer 530 and the first hydrophobic layer 540 are sequentially stacked on the first substrate 510, and for example, can be processed by spin coating or other methods. The first insulating layer 530 provides functions such as insulation and protection, and may use materials such as resin and silicon nitride. The first hydrophobic layer 540 has characteristics of hydrophobicity and lipophilicity, and therefore facilitates the movement of the liquid drop on the surface thereof. The first hydrophobic layer 540 may use materials such as Teflon or other suitable materials.

The plurality of driving electrodes 212 are disposed on a side, close to the second substrate 520, of the first substrate 510, and is covered by the first insulating layer 530 and the first hydrophobic layer 540. The driving electrode 212 can be obtained through, for example, a micro-electro-mechanical system (MEMS) process. The driving electrode 212 may use a transparent conductive material such as indium tin oxide (ITO), indium zinc oxide (IZO), etc., or may use a metal material, and the embodiments of the present disclosure are not limited in this aspect. The plurality of driving electrodes 212 may receive a plurality of driving signals S1, S2, and S3, respectively, so as to drive the liquid drop 400 to move.

The driving unit 210 further includes a second insulating layer 550, a common electrode layer 560, and a second hydrophobic layer 570. The second insulating layer 550, the common electrode layer 560, and the second hydrophobic layer 570 are sequentially stacked on the second substrate 520, and the second hydrophobic layer 570 is closer to the first substrate 510. The common electrode layer 560 is used to provide a common voltage Com to cooperate with the driving electrode 212, so as to implement a function of driving the liquid drop 400 to move. For example, the common electrode layer 560 may be grounded, or may also be connected to any applicable high-voltage terminal or low-voltage terminal, and the embodiments of the present disclosure are not limited in this aspect. The common electrode layer 560 may use a transparent conductive material, such as ITO, IZO, etc., or may use a metal material, and the embodiments of the present disclosure are not limited in this aspect. In a case where the common electrode layer 560 uses the transparent conductive material and the second substrate 520 is the transparent substrate, the chip 100 can be directly used for subsequent optical detection, thereby eliminating the collecting process of the liquid drop. The second insulating layer 550 is similar to the first insulating layer 530, the second hydrophobic layer 570 is similar to the first hydrophobic layer 540, and details are not described herein again.

For example, the chip 100 further includes a plurality of temperature control components, and each of the temperature control components includes a heating electrode 580 and a temperature sensing electrode 590.

Figure 4:
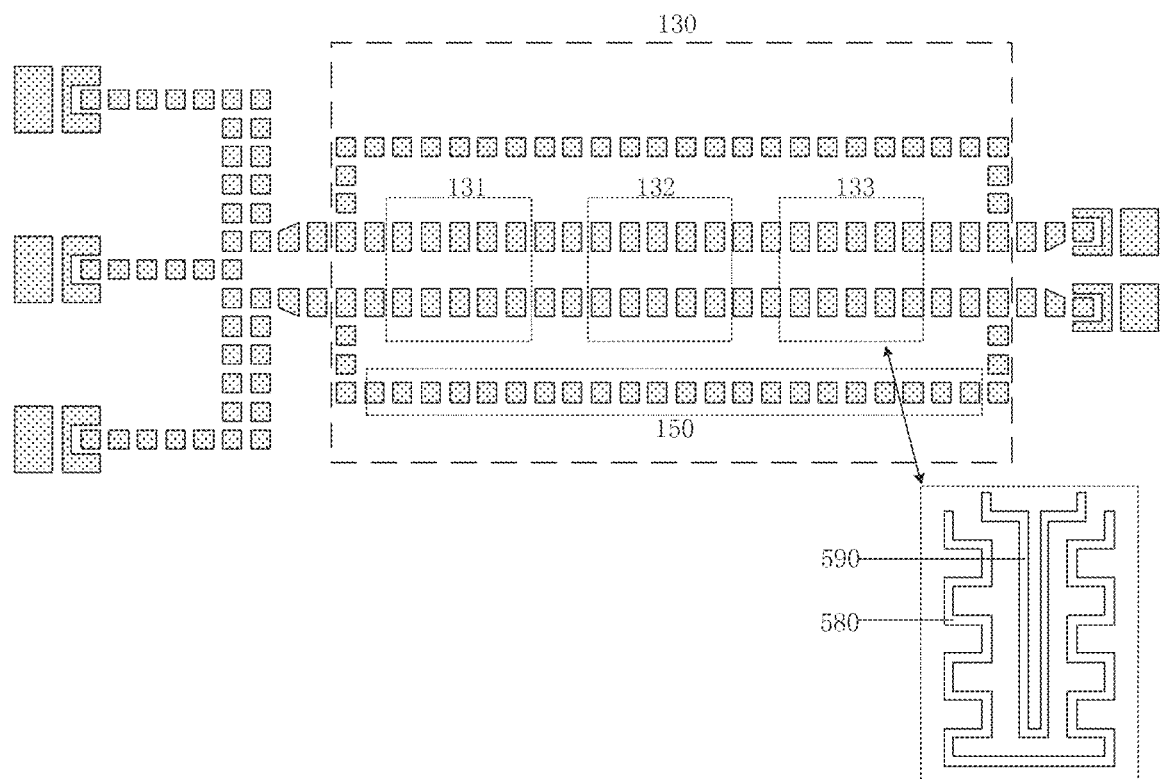
FIG. 4 is a schematic diagram of positions of a heating electrode and a temperature sensing electrode of a chip provided by an embodiment of the present disclosure.

For example, the heating electrode 580 is disposed on the second substrate 520 or the first substrate 510 and is configured to release heat. For example, in an example, the heating electrode 580 is disposed on the second substrate 520 and is covered by the second insulating layer 550. The heating electrode 580 is located in the temperature cycling region 130. For example, in an example, the shape and position of the heating electrode 580 are illustrated in FIG. 4. The temperature cycling region 130 includes the plurality of temperature regions in a sequential arrangement, and for example, includes the first temperature region 131, the second temperature region 132, and the third temperature region 133. Accordingly, the plurality of temperature control components include a first temperature control component, a second temperature control component, and a third temperature control component. The first temperature control component is located in the first temperature region 131 and is configured to maintain the first temperature region 131 at the first temperature (e.g., about 95° C.), so as to enable the gene segment in the liquid drop 400 to be annealed. The second temperature control component is located in the second temperature region 132 and is configured to maintain the second temperature region 132 at the second temperature (e.g., about 65° C.), so as to enable the gene segment in the liquid drop 400 to refold. The third temperature control component is located in the third temperature region 133 and is configured to maintain the third temperature region 133 at the third temperature (e.g., about 72° C.), so as to enable the gene segment in the liquid drop 400 to extend. Because each temperature control component includes the heating electrode 580, there are one or more heating electrodes 580 in each of the first temperature region 131, the second temperature region 132, and the third temperature region 133 for heating each of the temperature regions, respectively.

It should be noted that, in the embodiments of the present disclosure, a part of the driving units 210 of the driving unit group 211 are located in the temperature cycling region 130, and are located outside the first temperature region 131, the second temperature region 132, and the third temperature region 133, so as to form a cooling region 150 as illustrated in FIG. 4. That is, in a case where the liquid drop cyclically moves along the first loop 311 illustrated in FIG. 2, the liquid drop sequentially passes through the first temperature region 131, the second temperature region 132, and the third temperature region 133, and then returns through the cooling region 150. In this way, the liquid drop can be cooled in the cooling region 150 after one temperature cycling amplification process, thereby facilitating the start of the next temperature cycling amplification process. For example, there is no heating electrode 580 in the cooling region 150. The cooling region 150 is cooled by, for example, air cooling, a cooling liquid, or other applicable methods, and the embodiments of the present disclosure are not limited in this aspect.

For example, as illustrated in FIG. 4, the heating electrode 580 is in a broken line shape, such as an S-shaped broken line, a Z-shaped broken line, or a bow-shaped broken line. By setting the heating electrode 580 in a broken line shape, greater heating power can be provided in the smallest possible area, thereby increasing the heating speed and reducing the size of the chip 100. Certainly, the embodiments of the present disclosure are not limited in this aspect, and the shape of the heating electrode 580 may be any shape such as a straight line shape or a curved line shape, as long as satisfying the required heating power.

For example, the heating electrode 580 can be obtained by a sputtering process, an etching process, etc. The heating electrode 580 may use a transparent conductive material, such as ITO, IZO, etc., or may use a metal material, such as chromium, and the embodiments of the present disclosure are not limited in this aspect. In a case where the heating electrode 580 uses the transparent conductive material, the second substrate 520 is the transparent substrate, and the common electrode layer 560 also uses the transparent conductive material, the chip 100 can be directly used for subsequent optical detection, thereby eliminating the collecting process of the liquid drop.

For example, the heating electrode 580 may be electrically connected to a separately provided temperature control unit (not illustrated in the figure). The temperature control unit includes a temperature control circuit, and for example, the temperature control circuit provides a working voltage V1 to the heating electrode 580 according to a control signal, thereby controlling the heating electrode 580 to generate Joule heat. The manner of controlling the heating electrode 580 can be referred to the general heating circuit, which is not described in detail here.

For example, the temperature sensing electrode 590 is disposed on the second substrate 520 or the first substrate 510 and is configured to sense a temperature. For example, in an example, the temperature sensing electrode 590 is disposed on the second substrate 520 and is covered by the second insulating layer 550. The temperature sensing electrode 590 is located in the temperature cycling region 130. For example, in an example, the shape and position of the temperature sensing electrode 590 are illustrated in FIG. 4. The first temperature control component, the second temperature control component, and the third temperature control component are located in the first temperature region 131, the second temperature region 132, and the third temperature region 133, respectively. Because each temperature control component includes the temperature sensing electrode 590, each of the first temperature region 131, the second temperature region 132, and the third temperature region 133 has one temperature sensing electrode 590 for sensing the temperature of each temperature region.

For example, the temperature sensing electrode 590 is insulated from the heating electrode 580. In one same temperature control component, the temperature sensing electrode 590 is located in a pattern (for example, as illustrated in FIG. 4) formed by the heating electrode 580. By disposing the temperature sensing electrode 590 in the pattern formed by the heating electrode 580, the temperature sensed by the temperature sensing electrode 590 can be more accurate, thereby allowing the error between the sensed temperature and the actual temperature of the temperature region to be smaller.

For example, the temperature sensing electrode 590 may be in a broken line shape, a straight line shape, a curved line shape or any other shape, and the embodiments of the present disclosure are not limited in this aspect. For example, the temperature sensing electrode 590 can be obtained by a sputtering process. For example, the temperature sensing electrode 590 may use a transparent conductive material, such as ITO, IZO, etc., or may use a metal material, such as chromium, and the embodiments of the present disclosure are not limited in this aspect. In a case where the temperature sensing electrode 590 uses the transparent conductive material, the second substrate 520 is the transparent substrate, and the common electrode layer 560 and the heating electrode 580 also use the transparent conductive material, the chip 100 can be directly used for subsequent optical detection, thereby eliminating the collecting process of the liquid drop.

For example, the temperature sensing electrode 590 may be electrically connected to a separately provided temperature control unit (not illustrated in the figure). The temperature control unit includes a temperature detection circuit, and the temperature detection circuit acquires sensing signals S4 and S5 at two terminals of the temperature sensing electrode 590, thereby obtaining the temperature of the corresponding region through processing and calculation. For example, the temperature control unit may further include a calculation circuit (a processor), a memory, etc., which may be used for calculating and storing the temperature value and further provide the temperature value to other components for use. The manner of detecting the temperature by using the temperature sensing electrode 590 can be referred to the general temperature detection circuit, which is not described in detail here.

The heating electrode 580 and the temperature sensing electrode 590 cooperate with each other, and the separately provided temperature control unit is adopted, so that a temperature control function is implemented. For example, in a case where the temperature detected by the temperature sensing electrode 590 is lower than a predetermined temperature, the heating electrode 580 is controlled to provide heat; and in a case where the temperature reaches the predetermined temperature, the heating electrode 580 is controlled to maintain heat. In a case where the temperature detected by the temperature sensing electrode 590 is higher than the predetermined temperature, the heating electrode 580 is controlled to stop heating or stop maintaining heat, and a separately provided cooling device (such as an air cooling device) is used for cooling until the temperature reaches the predetermined temperature.

The chip 100 uses the structure as illustrated in FIG. 3 and FIG. 4, so that in a case where the liquid drop can be normally driven, the temperature control and temperature sensing are integrated in the chip 100, thereby effectively avoiding mutual interference with the driving signals applied to the driving electrodes 212 of the driving units 210, simplifying the complexity of the control system, reducing the manufacturing cost, and improving the integration of the system.

Figure 5:
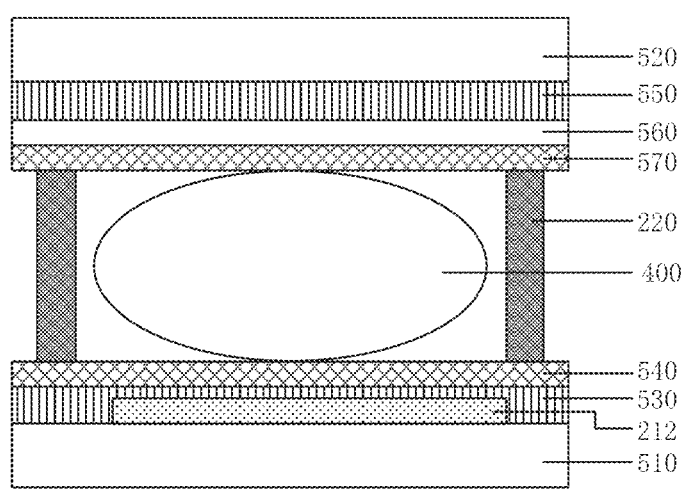
FIG. 5 is another cross-sectional diagram of the chip in FIG. 2 along a B-B' direction provided by an embodiment of the present disclosure.

FIG. 5 is another cross-sectional diagram of the chip in FIG. 2 along a B-B' direction provided by an embodiment of the present disclosure. Similarly, the liquid drop is illustrated in the figure for convenience of description. As illustrated in FIG. 5, in addition to including a flowing channel 220, a chip 200 is basically the same as the chip 100 illustrated in FIG. 3. It should be noted that the differences of the driving electrode 212, the heating electrode 580, and the temperature sensing electrode 590 in FIG. 5 from those in FIG. 3 are caused by different section positions of the cross-sectional diagrams, and are not the differences in structure between the chip 200 and the chip 100.

For example, the flowing channel 220 is located between the first substrate 510 and the second substrate 520, and is disposed along the liquid drop moving path formed by the plurality of driving electrodes 212. For example, the flowing channel 220 is used to provide a moving channel for the liquid drop, so as to provide physical isolation and physical protection to prevent cross-contamination between different liquid drops and providing support. The flowing channel 220 may use any suitable materials, such as an optical adhesive, a resin, etc., and for example, may be formed in the form of a division wall.

It should be noted that, in the embodiments of the present disclosure, the sizes of the chip 100 or the chip 200 and each component are not limited, and can be determined according to practical requirements. For example, in an example, the chip 100 illustrated in FIG. 1 and FIG. 3 may be designed as follows. The chip 100 has a length of 12 cm and a width of 6 cm. An electrode line width of the heating electrode 580 is 150 μm, and a thickness of the heating electrode 580 is 200 nm. An electrode line width of the temperature sensing electrode 590 is 50 μm and a thickness of the temperature sensing electrode 590 is 200 nm. By designing the temperature sensing electrode 590 as a thin layer electrode, it can be ensured that the temperature distribution of the surface may not be affected during temperature measurement. A resistance of the temperature sensing electrode 590 changes linearly at different temperatures, and for example, the effective measurement range is 50° C. to 150° C., which can accurately indicate the temperature change of each temperature region in the temperature cycling region 130. A height between the first substrate 510 and the second substrate 520 is 150 μm.

Figure 6:
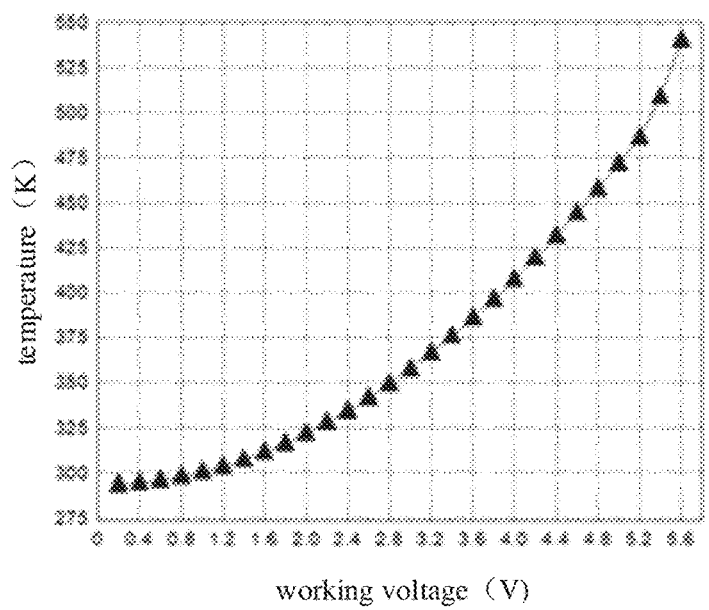
FIG. 6 is a schematic diagram of a curve of a working voltage of a heating electrode with respect to a working region temperature of a chip provided by an embodiment of the present disclosure.

For example, in order to optimize temperature control, the finite element analysis (FEA) method is used to simulate the thermal effect of the chip 100 illustrated in FIG. 3 and FIG. 4. In a case where the heating electrode 580 uses the sizes described above, that is, in a case where the electrode line width of the heating electrode 580 is 150 μm and the thickness of the heating electrode 580 is 200 nm, a curve of the working voltage of the heating electrode 580 as illustrated in FIG. 6 with respect to the working region temperature is obtained. In a case where the environmental temperature is set to 293.15 K (that is, 20° C.), the heating electrode 580 is considered as an internal electromagnetic heat source, and the working voltage of the heating electrode 580 is in positive correlation with the working region temperature in a case where heat conduction and heat radiation of the first substrate 510 and each film layer thereon, and the second substrate 520 and each film layer thereon are considered. Therefore, the working region temperature can be controlled by controlling the working voltage of the heating electrode 580, and the positive correlation between the working region temperature and the working voltage of the heating electrode 580 can facilitate improving the precision and accuracy of the control.

Figure 7:
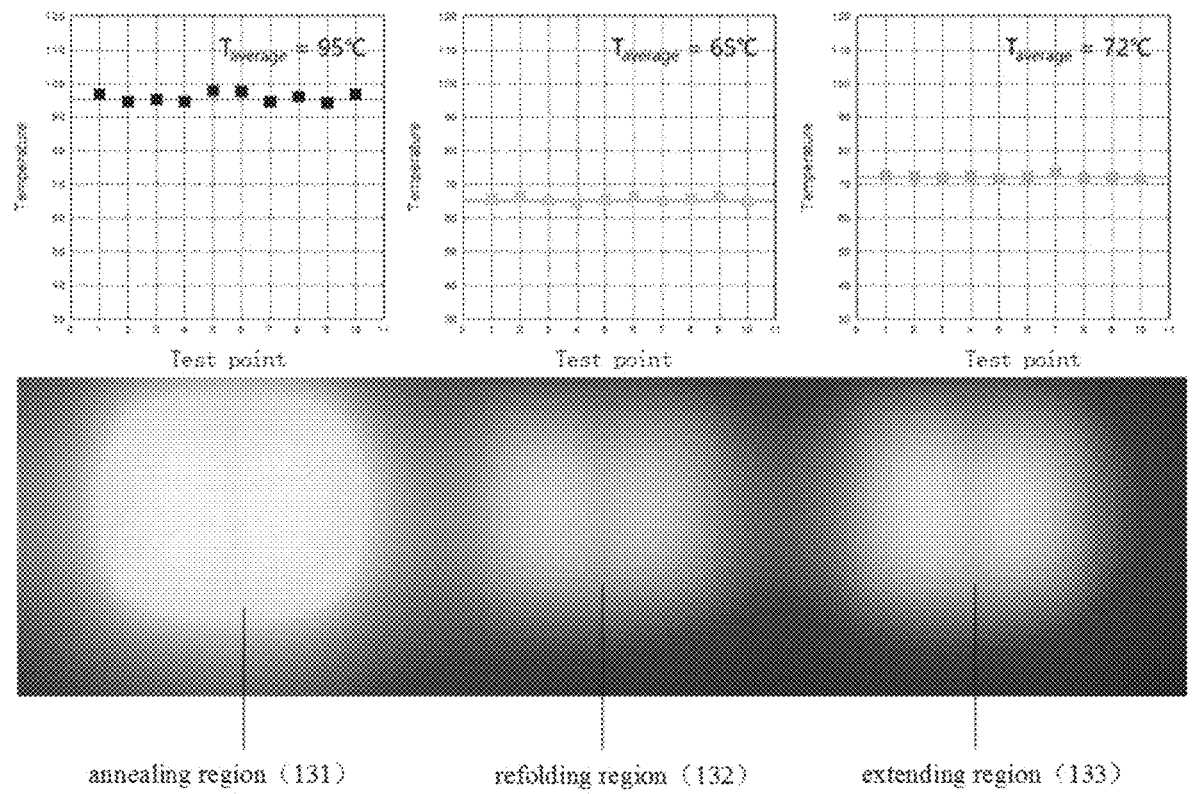
FIG. 7 is a schematic diagram of a region temperature distribution of a chip provided by an embodiment of the present disclosure.

For example, the temperature distribution of the temperature cycling region 130 of the chip 100 illustrated in FIG. 3 and FIG. 4 is simulated by using the FEA method, and a temperature distribution diagram as illustrated in FIG. 7 is obtained. As illustrated in FIG. 7, average temperatures $T_{average}$ of the liquid drop in an annealing region (i.e., the first temperature region 131), a refolding region (i.e., the second temperature region 132), and an extending region (i.e., the third temperature region 133) are 95° C., 65° C. and 72° C., respectively. For example, a thermal conductivity of the liquid drop is 0.55 W/(m*K), which is greater than a thermal conductivity of the fluorinated oil. It can be seen from FIG. 7 that different temperature regions maintain a certain distance, which can avoid temperature interference with each other. The simulation result takes into consideration the natural thermal convection of the first substrate 510 and the second substrate 520 from the external environment, thereby ensuring the temperature consistency under the steady state condition. In addition, temperatures of 10 points in each temperature region are randomly selected and calculated, and the difference between the temperature of each point and the average value is within 2° C., which indicates that the temperature uniformity in each temperature region is good, thereby ensuring the stability and reliability of the amplification process.

At least one embodiment of the present disclosure further provides a reaction device, which includes the chip provided by any one of the embodiments of the present disclosure, and further includes a control unit. The control unit is configured to apply electric signals to driving electrodes of the driving units to control the liquid drop to move. The reaction device allows processes such as sample mixing, temperature cycling amplification, and product collection during nucleic acid amplification to be integrated, thereby lowering requirements for experimental environment, reducing manual operations, providing a flowing temperature cycling function, simplifying a system structure and an apparatus volume, reducing operating costs, and contributing to implementation of real time detection.

Figure 8:
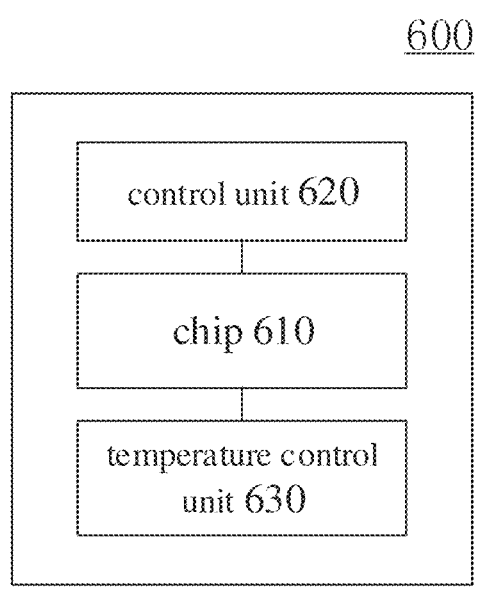
FIG. 8 is a schematic block diagram of a reaction device provided by an embodiment of the present disclosure.

FIG. 8 is a schematic block diagram of a reaction device provided by an embodiment of the present disclosure. As illustrated in FIG. 8, a reaction device 600 includes a chip 610 and a control unit 620. The chip 610 is the chip 100/200 according to any one of the embodiments of the present disclosure. The control unit 620 is electrically connected to the driving electrodes 212 of the plurality of driving units 210 in the chip 610, and is configured to apply electrical signals to the driving electrodes 212 to control the liquid drop to move. For example, the driving electrodes 212 can be used to control the liquid drop to move by using the general electro-wetting method. Therefore, the electrical signals applied to the driving electrodes 212 by the control unit 620 can be referred to the conventional design, which are not described in detail here. The reaction device 600 may be a PCR amplification system or any other devices, and the embodiments of the present disclosure are not limited in this aspect.

For example, in an example, the reaction device 600 further includes a temperature control unit 630. The temperature control unit 630 is configured to acquire a detection signal of the temperature sensing electrode 590 of the chip 610 and control a working state of the heating electrode 580 of the chip 610, so as to implement temperature control. For example, the temperature control unit 630 is electrically connected to the temperature sensing electrode 590 and the heating electrode 580, so as to acquire the detection signal of the temperature sensing electrode 590 and apply the working voltage to the heating electrode 580. For example, the temperature control unit 630 may include a temperature control circuit, a temperature detection circuit, a calculation circuit (such as a processor), etc. The temperature control circuit is used to apply the working voltage to the heating electrode 580, the temperature detection circuit is used to detect the detection signal of the temperature sensing electrode 590, and the calculation circuit is used to calculate the temperature value and determine the working voltage to be applied according to the temperature value.

For example, the control unit 620 and the temperature control unit 630 may be implemented as specific or general electronic hardware (or circuits), and the embodiments of the present disclosure are not limited in this aspect. The specific structure of the electronic hardware is not limited, and may include an analog device, a digital chip, or other applicable components. It should be noted that, in the embodiments of the present disclosure, the reaction device 600 may further include more or fewer components, which may be determined according to practical requirements, and the embodiments of the present disclosure are not limited in this aspect. The technical effects of the reaction device 600 can be referred to the above description of the chip 100/200, which are not described in detail here.

At least one embodiment of the present disclosure further provides a method of operating the chip according to any one of the embodiments of the present disclosure. The method can be used to operate the chip according to the embodiments of the present disclosure, thereby allowing processes such as sample mixing, temperature cycling amplification, and product collection during nucleic acid amplification to be integrated, lowering requirements for experimental environment, reducing manual operations, providing a flowing temperature cycling function, simplifying a system structure and an apparatus volume, reducing operating costs, and contributing to implementation of real time detection.

For example, in an example, the method of operating the chip includes the following operation: applying electric signals to the driving electrodes 212 of the driving units 210 to allow the liquid drop to move and sequentially pass through the sample adding region 110, the mixing region 120, and the temperature cycling region 130.

For example, in another example, the method of operating the chip further includes the following operation: using the temperature sensing electrode 590 of the chip 100/200 to detect temperatures of a plurality of temperature regions in the temperature cycling region 130, and controlling a working state of the heating electrode 580 of the chip 100/200 to allow the temperatures of the plurality of temperature regions to reach predetermined temperatures, respectively.

For example, the predetermined temperatures are temperatures at which the gene segment in the liquid drop is enabled to be annealed, to refold and to extend, respectively.

The details and technical effects of the method can be referred to the above description of the chip 100/200 and the reaction device 600, which are not described in detail here.

The following statements should be noted.

(1) The accompanying drawings involve only the structure(s) in connection with the embodiment(s) of the present disclosure, and other structure(s) can be referred to common design(s).

(2) In case of no conflict, features in one embodiment or in different embodiments can be combined to obtain new embodiments.

What have been described above are only specific implementations of the present disclosure, the protection scope of the present disclosure is not limited thereto, and the protection scope of the present disclosure should be based on the protection scope of the claims.

What is claimed is:

1. A reaction device, comprising a chip for polymerase chain reaction and a control unit, wherein the chip for polymerase chain reaction, comprising:
a sample adding region, a mixing region, and a temperature cycling region in a sequential arrangement wherein the sample adding region is configured to add a sample, for separating a sample liquid and a reaction system liquid which are stored in a liquid container into liquid drops, the mixing region is configured to allow the liquid drop from the sample liquid to be mixed with the liquid drop from the reaction system liquid, the temperature cycling region is configured to is configured to allow the liquid drop of the reaction liquid to perform an annealing-refolding-extending temperature cycling amplification process, so as to perform the amplification reaction; and
at least one driving unit group, wherein the at least one driving unit group comprises a plurality of driving units, and is configured to drive a liquid drop to move and sequentially pass through the sample adding region, the mixing region, and the temperature cycling region, the sample adding region, the mixing region and the temperature cycling region is arranged in a moving direction of the liquid drop, the plurality of driving unit comprising driving electrodes,
each of the at least one driving unit group comprises: a first driving unit sub-group, in the temperature cycling region and configured to drive the liquid drop to cyclically move in the temperature cycling region; and a second driving unit sub-group, in the mixing region and configured to drive the liquid drop to cyclically move in the mixing region, and the second driving unit sub-group comprises the driving units arranged in a ring to form a loop.

2. The reaction device according to claim 1, wherein each of the at least one driving group further comprises a third driving unit sub-group, in the sample adding region and configured to drive the liquid drop to move in the sample adding region.

3. The reaction device according to claim 1, wherein the first driving unit sub-group comprises a plurality of driving units arranged in a ring.

4. The reaction device according to claim 1, further comprising at least one first liquid container and at least one second liquid container,
wherein the first liquid container and the second liquid container are in the sample adding region, and are configured to store different liquids and provide the liquid drop.

5. The reaction device according to claim 4, wherein the at least one driving unit group comprises a first driving unit group and a second driving unit group, and the first driving unit group and the second driving unit group are configured to obtain the liquid drop from the first liquid container.

6. The reaction device according to claim 4, wherein the second driving unit sub-group is further configured to allow a first liquid drop from the first liquid container to be mixed with a second liquid drop from the second liquid container.

7. The reaction device according to claim 1, wherein the driving unit comprises:
a first substrate and a second substrate opposite to each other, wherein a flowing space for the liquid drop is between the first substrate and the second substrate; and
a driving electrode on the first substrate.

8. The reaction device according to claim 7, wherein the driving unit further comprises a first insulating layer and a first hydrophobic layer,
wherein the first insulating layer and the first hydrophobic layer are sequentially stacked on the first substrate in a direction perpendicular to the first substrate, and the driving electrode is on a side, close to the second substrate, of the first substrate, and is covered by the first insulating layer and the first hydrophobic layer.

9. The reaction device according to claim 8, wherein the driving unit further comprises a second insulating layer, a common electrode layer, and a second hydrophobic layer,
the second insulating layer, the common electrode layer, and the second hydrophobic layer are sequentially stacked on the second substrate in a direction perpendicular to the second substrate, and the second hydrophobic layer is closer to the first substrate, the common electrode layer is configured to provide a common voltage to cooperate with the driving electrode to drive the liquid drop to move.

10. The reaction device according to claim 7, further comprising a plurality of temperature control components, wherein the plurality of temperature control components comprise a first temperature control component, a second temperature control component, and a third temperature control component, the temperature cycling region comprises a plurality of temperature regions in a sequential arrangement in the moving direction of the liquid drop, the plurality of temperature regions comprise a first temperature region, a second temperature region, and a third temperature region,
the first temperature control component is in the first temperature region and is configured to allow the first temperature region to stay at a first temperature, so as to enable a gene segment in the liquid drop to be annealed,
the second temperature control component is in the second temperature region and is configured to allow the second temperature region to stay at a second temperature, so as to enable the gene segment in the liquid drop to refold, and
the third temperature control component is in the third temperature region and is configured to allow the third temperature region to stay at a third temperature, so as to enable the gene segment in the liquid drop to extend.

11. The reaction device according to claim 10, wherein each of the temperature control components comprises a heating electrode and a temperature sensing electrode,
the heating electrode is on the second substrate or the first substrate and is configured to release heat, and the temperature sensing electrode is on the second substrate or the first substrate and is configured to sense a temperature.

12. The reaction device according to claim 11, wherein the heating electrode is in a broken line shape, the broke line shape comprises at least a first sub-line and a second first sub-line, the first sub-line and the second sub-line intersect and extend in different directions.

13. The reaction device according to claim 11, wherein the temperature sensing electrode is insulated from the heating electrode.

14. The reaction device according to claim 10, wherein a part of the plurality of driving units of the driving unit group are in the temperature cycling region, and are outside the first temperature region, the second temperature region, and the third temperature region.

15. The reaction device according to claim 1, further comprising a liquid collecting region,
wherein the at least one driving unit group is further configured to drive the liquid drop to move into the liquid collecting region after the liquid drop passes through the temperature cycling region.

16. The reaction device according to claim 7, wherein the second substrate is a transparent substrate.

17. The reaction device according to claim 1, further comprising a temperature control unit,
wherein the temperature control unit is configured to acquire a detection signal of a temperature sensing electrode of the chip and control a working state of a heating electrode of the chip, so as to implement temperature control.

18. A method of operating the chip according to claim 1, comprising:
applying electric signals to driving electrodes of the driving units to allow the liquid drop to move and sequentially pass through the sample adding region, the mixing region, and the temperature cycling region.

19. The method according to claim 18, further comprising:
using a temperature sensing electrode of the chip to detect temperatures of a plurality of temperature regions in the temperature cycling region, and controlling a working state of a heating electrode of the chip to allow the temperatures of the plurality of temperature regions to reach predetermined temperatures, respectively.

\* \* \* \* \*